US005470957A

United States Patent [19]

Reed

[11] Patent Number: 5,470,957
[45] Date of Patent: Nov. 28, 1995

[54] IMMUNOINHIBITORS OF FACTOR XIII

[75] Inventor: Guy Reed, Winchester, Mass.

[73] Assignees: President and Fellows of Harvard College, Cambridge; The General Hospital Corporation, Boston, both of Mass.

[21] Appl. No.: 131,199

[22] Filed: Oct. 1, 1993

[51] Int. Cl.$^6$ .................. A61K 39/395; C07K 16/36; C07K 16/18
[52] U.S. Cl. .................. 530/388.25; 530/388.1; 424/145.1; 424/158.1; 435/172.2; 435/240.27
[58] Field of Search .............. 435/70.21, 172.2, 435/240.27; 530/387.1, 388.1, 388.25; 424/141.1, 145.1, 158.1

[56] References Cited

FOREIGN PATENT DOCUMENTS 9215609 9/1992 WIPO .................. C07K 7/00

OTHER PUBLICATIONS

Fukue et al., A Unique Factor XIII Inhibitor to a Fibrin–Binding Site on Factor XIIIA, Blood 79:65–74, 1992.
Gailani, An IgG Inhibitor Against Coagulation Factor XIII: Resolution of Bleeding after Plasma Immunoadsorption with Staphylococcal Protein A, Am. J. Medicine 92:110–112, 1992.
Galfre et al., Antibodies to Major Histocompatibility Antigens Produced by Hybrid Cell Lines, Nature 266:550–552, 1977.
Godal and Ly, An Inhibitor of Activated Factor XIII, Inhibiting Fibrin Cross–Linking but not Incorporation of Amine into Casin, Scand. J. Haemotol. 19:443–448, 1977.
Godal, An Inhibitor of Fibrin Stabilizing Factor (FSF, Factor XIII), Scand. J. Haemtol. 7:43–48, 1970.
Greenberg et al., Regulation of Thrombin Cleavage of Plasma Factor XIII Bound to Fibrin, Annals of The New York Academy of Sciences 485:140–143.
Janus et al., Promotion of Thrombin–Catalyzed Activation of Factor XIII by Fibrinogen, Biochemistry 27:6269–6272, 1983.
Krumdieck et al., Hemorrhagic Disorder Due to an Isoniazid-Associated Acquired Factor XIII inhibitor in a Patient with Waldenström's Macroglobulinemia, Am. J. Medicine 90:639–645, 1991.
Lewis et al., An Acquired Inhibitor to Coagulation Factor XIII, The Johns Hopkins Medical Journal 120:401–407, 1967.
Lopaciuk et al., Differences Between Type I Autoimmune Inhibitors of Fibrin Stabilization in Two Patients with Servere Hemorrhagic Disorder, J. Clin. Invest. 61:1196–1203, 1978.
Lorand et al., Autoimmune Antibody (IgG Kansas) Against the Fibrin Stablizing Factor (Factor XIII) System, Proc. Natl. Acad. Sci. USA 85:232–236, 1988.
Lorand et al., A Filter Paper Assay for Transamidating Enzymes Using Radioactive Amine, Substrates, Analytical Biochemistry 50:623–631, 1972.
Lukacova and Reed, Single Step Purification of Platelet Factor XIII Using an Immobulized Factor XIII A–Subunit Monoclonal Antibody, Thrombosis and Haemostasis 69:397–400, 1993.
Lukacova et al., Inhibition of Factor XIII Activation by an Anti–Peptide Monoclonal Antibody, Biochemistry 30:10164–10170, 1991.
Lukacova et al., Functional Characteristics of a Monoclonal Antibody Directed to the Thrombin Activation Site of Factor XIII, FASEB J. 5:A515 (Abstract #837), 1991.
Lynch et al., Monoclonal Antibodies to Factor XIII, Thrombosis and Haemostasis 54:274 (Abstract #01627) 1985.
McDevitt et al., An Acquired Inhibitor to Factor XIII, Arch. Intern Med 130:772–777, 1972.
Milner et al., Practolol Therapy Associated with a Systemic Lupus Erythematosus–Like Syndrome and an Inhibitor to Factor XIII, J. Clin. Path. 30:770–773, 1977.
Nakamura et al., Bleeding Tendency Caused by IgG Inhibitor to Factor XIII, Treated Successfully by Cyclophosphamide, British J. Haematology 68:313–319, 1988.
Naski et al., Characterization of the Kinetic Pathway for Fibrin Promotion of α–Thrombin–Catalyzed Activation of Plasma Factor XIII, Biochemistry 30:934–941, 1991.
Otis et al., An Acquired Inhibitor of Fibrin Stabilization Associated with Isoniazid Therapy: Clinical and Biochemical Observations, Blood 44:771–781, 1974.
Reed et al., Synergistic Fibinolysis: Combined Effects of Plasminogen Activators and an Antibody that Inhibits α2–antiplasmin, Proc. Natl. Acad. Sci. USA 87:1114–1118, 1990.
Rosenberg et al., A New Haemorrhagic Disorder with Defective Fibrin Stabilization and Cryofibrinogenaemia, British Journal of Haematology 26269–284, 1974.
Sakata and Aoki, Cross–Linking of α2–Plasmin Inhibitor to Fibrin by Fibrin–stablizing Factor, J. Clin. Invest. 65:290–297, 1980.
Schlaeger and Schumpp, Propagation of a Mouse Myeloma Cell Line J558L Producing Human CD4 Immunoglobulin G1, J. Immunological Methods 146111–120, 1992.
Shebuski et al., Inhibition of Factor XIIIa in a Canine Model of Coronary Thrombosis: Effect on Reperfusion and Acute Reocclusion After Recombinant Tissue–Type Plasminogen Activator, Blood 75:1455–1459, 1990.

Primary Examiner—David L. Lacey
Assistant Examiner—Phillip Gambel
Attorney, Agent, or Firm—Fish & Richardson

[57] ABSTRACT

Novel immunoinhibitors are capable of inhibiting thrombin-activated function of Factor XIII by binding to Factor XIII at a site other than the thrombin-cleavage site of Factor XIII.

2 Claims, 5 Drawing Sheets

IMMUNOINHIBITORS OF FACTOR XIII

STATEMENT AS TO FEDERALLY SPONSORED RESEARCH

This invention was supported in part by grant K08, HL02348 from the National Institutes of Health. The U.S. Government therefore has certain rights in the invention.

FIELD OF THE INVENTION

This invention relates; to inhibition of blood clot formation.

BACKGROUND OF THE INVENTION

Factor XIII (FXIII) is the final enzyme in the blood coagulation cascade. In blood, FXIII is present in two forms. Plasma FXIII is produced in the liver and exists as a heterotetramer with two catalytic α-subunits and two non-catalytic β-subunits (α2β2) (Schwartz M. L., Pizzo S. V., Hill R. L., McKee P. A.: Human factor XIII from plasma and platelets: Molecular weights, subunit structure, proteolytic activation and crosslinking of fibrinogen and fibrin. J. Biol. Chem. 248:1395, 1973). Platelet FXIII is made up of only two α-subunits (α2). α2 is also found intracellularly in megakaryocytes, monocytoid cells, and cells of the placenta (Schwartz et al., supra; Henriksson P., Becker S., Lynch G., McDonagh J.: Identification of intracellular factor XIII in human monocytes and macrophages. J. Clin. Invest. 76: 528, 1985). When activated, FXIII plays a critical role in thrombosis by cross-linking $\alpha_2$-antiplasmin to fibrin and fibrin chains to one another.

Two types of enzymatic processes contribute to the formation of a blood clot. The first process involves zymogen and cellular activation and is mediated by thrombin and other serine proteases of the coagulation system. The second process involves the intermolecular cross-linking of fibrin and other proteins and is catalyzed by the transglutaminase, FXIII. These two processes converge in the clotting of fibrinogen.

Fibrinogen is cleaved by thrombin, resulting in the conversion of fibrinogen to the insoluble protein, fibrin, and the concomitant release of "activation peptides". Thrombin also cleaves an activation peptide from the α-subunit of FXIII, α2, to yield thrombin-cleaved α-subunit of FXIII (α2'), which then undergoes a conformational change to form the activated enzyme, α-subunit of FXIII (α2*) (Lorand L.: Activation of blood coagulation factor XIII. Ann. N.Y. Acad. Sci. 485:144, 1986). The α2* enzyme catalyzes the intermolecular formation of ε-(γ-glutamyl)lysine cross-links between adjacent fibrin gamma chains and between contiguous fibrin alpha chains (Chen R, Doolittle RT: Isolation, characterization and location of a donor-acceptor unit from cross-linked fibrin. Proc. Natl. Acad. Sci. U.S.A. 66:472, 1970; Pisano J. J., Bronzert T. J., Peyton M. P., Finlayson J. S.: ε-(γ-Glutamyl) lysine cross-links: determination in fibrin from normal and factor XIII-deficient individuals. Ann. N.Y. Acad. Sci. 202:98, 1972). Enzyme α2* also cross-links other plasma proteins, such as $\alpha_2$-antiplasmin (Tamaki T., Aoki N.: Cross-linking of -plasmin inhibitor and fibronectin to fibrin by fibrin-stabilizing factor. Biochim. Biophys. Acta 661:280, 1981) and fibronectin (Mosher D. F.: Cross-linking of cold-insoluble globulin by fibrin-stabilizing factor. J. Biol. Chem. 250:6614, 1975) to fibrin. The resulting fibrin mesh is resistant to mechanical or proteolytic disruption (Lorand L., Jacobsen A.: Accelerated lysis of blood clots. Nature 195:911, 1962).

SUMMARY OF THE INVENTION

Novel immunoinhibitors of the coagulation enzyme, FXIII, have now been identified. These unique immunoinhibitors are potent and specific for FXIII and are useful in the prevention of blood clot formation.

The invention features a purified preparation of a compound capable of inhibiting the function of FXIII by binding to FXIII at a site other than the thrombin-cleavage site of FXIII. By "purified preparation" is meant a compound which is separated from components of the cell or tissue in which it naturally occurs; preferably it is purified to represent at least 20%, more preferably at least 50%, more preferably at least 75%, and most preferably at least 90% of the total material by weight. By "function" of FXIII is meant the ability to catalyze the formation of a blood clot. By "thrombin-cleavage site" is meant the position of the FXIII zymogen, i.e., between $Arg_{37}$ and $Gly_{38}$, at which thrombin-catalyzed proteolysis occurs.

In another aspect, the invention features a monoclonal antibody (MAb) which is capable of inhibiting the function of FXIII by preventing the thrombin-cleavage of FXIII without binding to the thrombin-cleavage site of FXIII. The antibody is also capable of inhibiting the activity of FXIII which has been previously activated by thrombin cleavage. In preferred embodiments, the MAb is the MAb 9C11 or 10G10. The term "monoclonal antibody" is defined as an antibody that is produced by a homogenous cell line derived from a single antibody-producing hybridoma.

The invention encompasses not only an intact monoclonal antibody, but also an immunologically-active antibody fragment, e.g., a Fab or (Fab)₂ fragment; an engineered single chain Fv molecule; or a chimeric molecule, e.g., an antibody which contains the binding specificity of one antibody, e.g., of murine origin, and the remaining portions of another antibody, e.g., of human origin.

In a third aspect, the invention features a method of preventing coagulation of blood in which the FXIII-inhibitory antibody is introduced into blood.

In a fourth aspect, the invention features a method of preventing and/or lysing blood clots, by introducing into blood the FXIII-inhibitory antibody either, simultaneously or sequentially with a thrombolytic agent, e.g., a plasminogen activator, such as, tissue-type plasminogen activator, urokinase, prourokinase, streptokinase, staphylokinase or vampire bat tissue plasminogen activator. The thrombolytic agent to be co-administered with the MAb of the invention can be an active fragment of a thrombolytic agent, which fragment is derived from the native protein or recombinantly-produced, e.g., single chain urokinase plasminogen activator (scu-PA), or a hybrid thrombolytic agent, e.g., a thrombolytic agent or active fragment thereof linked by chemical or recombinant means to a molecule which can direct the thrombolytic agent to a thrombus, e.g, an antibody, such as a fibrin-specific or platelet-specific antibody.

In yet another aspect, the invention features a method of detecting FXIII in a sample, by contacting a sample with a MAb, e.g., 9C11 or 10G10, specific for the α-subunit of FXIII and determining whether the antibody binds. This method may also be used to characterize naturally-occurring immunoinhibitors by measuring their ability to compete with the MAbs of the invention for binding sites on FXIII.

In a final aspect, the invention features a method of screening a candidate compound for FXIII-inhibitory activity, by determining whether the binding of a FXIII-inhibitory MAb to FXIII, either before or after thrombin-catalyzed cleavage of FXIII, is altered in the presence of a candidate compound. A decrease in antibody binding in the presence of the candidate compound would indicate that the candidate compound competes with the FXIII-inhibitory antibody for binding to FXIII, and thus, is likely to inhibit the activity of FXIII.

DETAILED DESCRIPTION

Figure 1:
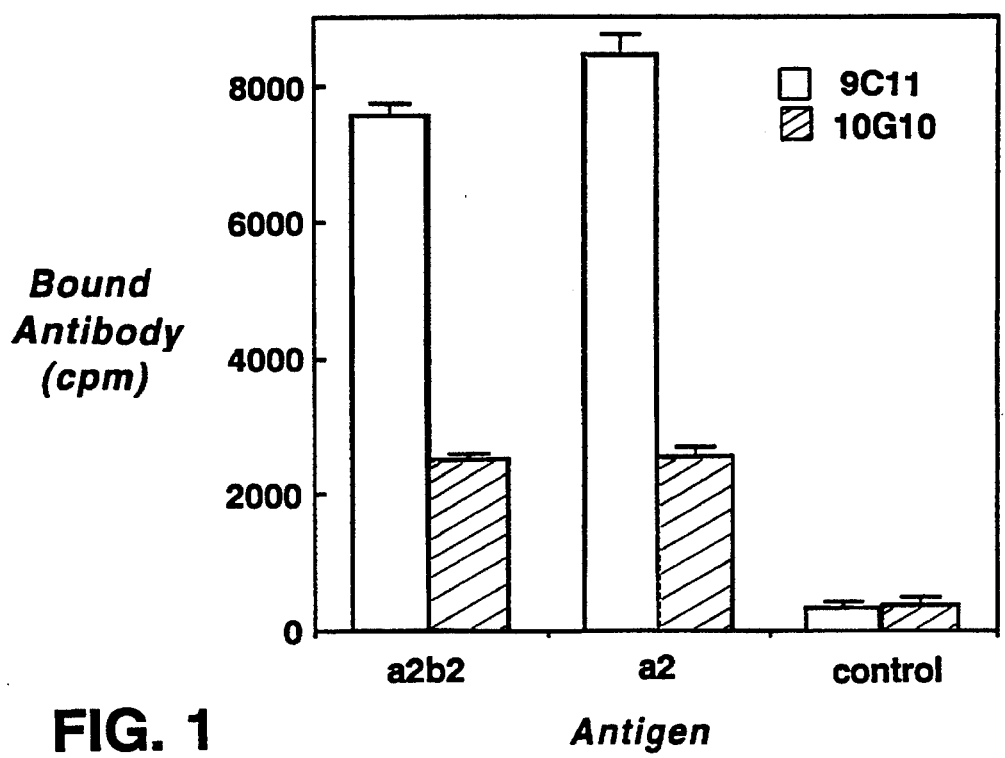
FIG. 1 is a bar graph showing the binding of MAbs to plasma FXIII, α2β2, or platelet FXIII, α2, or a negative control antigen, bovine serum albumin (BSA). Culture supernatants from MAbs 9C11 and 10G10 were added to wells of a microtiter plate coated with platelet or plasma FXIII or BSA. After washing, the amount of bound MAb was determined with a radiolabeled anti-mouse antibody.

The invention features novel compositions which are potent and specific immunoinhibitors of the coagulation enzyme, FXIII. These immunoinhibitors were found to be capable of quenching apparent FXIII activity against low molecular weight substrates such as $^{14}$C-putrescine. In addition, when incubated with plasma, the immunoinhibitors suppressed the cross-linking of fibrin gamma chains and accelerated the lysis of plasma clots. Studies with purified reagents confirmed that the two antibodies inhibited thrombin cleavage of FXIII during activation of the enzyme. Yet despite their similar mechanisms of action, the two antibodies tested bound to mutually exclusive sites on the FXIII molecule (largely outside the thrombin cleavage site) in competitive binding experiments. The MAbs, 9C11 and 10G10, represent the most potent and specific inhibitors of FXIII activation yet described. Such immunoinhibitors can be generated and identified using the methods described below.

Production of MAbs

Female BALB/C mice were initially immunized subcutaneously with 5 μg of α2 emulsified in complete Freund's adjuvant (Difco, Detroit, Mich.) and boosted with 5 μg of α2 at intervals at approximately 1, 6, and 8 months thereafter. The mice were hyperimmunized with 50 μg of α2 four days prior to sacrifice. Spleens were harvested from two mice, and somatic cell fusion of spleen cells to myeloma cells was performed according to methods well known in the art (Galfre G., Howe S. C., Milstein C., Butcher G. W., Howard J. C.: Antibodies to major histocompatibility antigens produced by hybrid cell lines. Nature 266:550, 1977). The ratio of myeloma cells (SP2/0) to spleen cells was 1:2.

Hybridomas producing antibody to α2 were identified using reverse solid-phase radioimmunoassay. In this assay, wells of a microtiter plate were coated with goat anti-mouse antibody (25 μl, 3 μg/ml) (Cappel, Malvern, Pa.) for five hours. Nonspecific binding sites were blocked with 200 μl of 1% BSA for at least one hour. Subsequently, hybridoma culture supernatants (25 μl) were added to the wells for 2 hours. After the wells had been washed, a 1:50 dilution of supernatant from sonicated human platelets (1×10$^{11}$ cells/ml) was added to each well as a source of α2. After 1 hour, the wells were washed and 25 μl of a 1:1000 dilution of rabbit anti-FXIII α2 (Diagnostica Stago, France) was added to detect bound α2.

Bound anti-α2 antibody was detected by the addition of $^{125}$I-protein A (50,000 cpm/25 μl). In the initial screen, 72 hybridomas were identified that produced antibody capable of capturing FXIII at levels significantly higher than those of a negative control MAb.

All antibodies were screened again using a conventional direct solid-phase assay. In this assay, wells of a microtiter plate were coated with 3 μg/ml of α2 (25 μl) and allowed to incubate overnight. Non-specific binding sites were blocked with a 1% BSA solution for 1 hour, followed by the addition of 25 μl of hybridoma supernatant to each well and incubation for 2 hours. Wells were washed and bound antibody was detected by the addition of $^{125}$I-goat anti-mouse antibody (25 μl, 50,000 cpm). An additional 30 hybridomas producing antibody to FXIII were identified in the second screen.

Based on strength and specificity of binding to FXIII, 67 cell lines were selected from these 102 hybridomas for further testing. The antibody-producing cell lines were cloned by limiting dilution and the isotype of each antibody determined using Zymed reagents (San Francisco, Calif.). Selected cell lines were inoculated into pristane-primed mice to induce the production of ascites fluid. MAbs were purified from ascitic fluid by protein A-agarose (Pierce, Rockford, Ill.) affinity chromatography.

α2-specific antibodies

After repeated and prolonged immunization and several somatic cell fusion experiments, two potent inhibitors of FXIII activity were identified. These immunoinhibitors were characterized with respect to their effect on FXIII activity against small- and large-molecule substrates, their mechanism of action, and their binding specificity on the FXIII molecule.

To obtain immunoinhibitors of FXIII, mice were immunized with α2β2. Somatic cell fusion with splenocytes from these mice yielded many anti-FXIII MAbs, but only one of the MAbs was specific for α2. To improve the yield of α2-specific antibodies, mice were immunized with α2 alone. Six fusion experiments generated more than 100 MAbs to α2, but nearly all of them had low binding affinities and were of the IgM isotype. After prolonged immunization, the predominant isotype switched from IgM to IgG. Somatic cell fusion was performed again resulting in 102 hybridomas (5% of wells) that produced antibody to α2, 67 of which were further evaluated.

Since these two MAbs (9C11 and 10G10) were raised in mice immunized with α2, they were tested for α2β2 binding in a direct solid-phase assay. FIG. 1 shows a comparison of the binding of these two MAbs to α2, α2β2, and a negative control antigen, BSA. Both 9C11 and 10G10 bound specifically to FXIII. In addition, each MAb appeared to bind nearly as well to α2β2 as it bound to α2 in this assay.

To further characterize the MAbs, the binding of 9C11 and 10G10 to denatured α2 was evaluated. α2 was subjected to sodium dodecyl sulfate-polyacrylamide gel electrophoresis (SDS-PAGE) under denaturing conditions, and then immunoblotted with 9C11 and 10G10. Neither MAb bound to denatured α2, indicating that they recognize conformationally dependent epitopes. Both 9C11 and 10G10 were found to be of the IgG1 kappa isotype.

Strain Deposit

Under the terms of the Budapest Treaty on the International Recognition of the Deposit of Microorganisms for the Purpose of Patent Procedure, hybridomas 9C11 and 10G10 have been deposited with the American Type Culture Collection (ATCC) of Rockville, Md., U.S.A., on Sep. 30, 1993. The two deposits have been given the ATCC designations American Type Culture Collection Designation CRL 11458 and American Type Culture Collection Designation CRL 11457, respectively.

Applicant's assignees, President and Fellows of Harvard College and The General Hospital Corporation, represent that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 U.S.C. §122. The deposited material will be maintained with all the care necessary to keep it viable and uncontaminated for a period of at least five years after the most recent request for the furnishing of a sample of the deposited plasmid, and in any case, for a period of at least thirty (30) years after the date of deposit or for the enforceable life of the patent, whichever period is longer. Applicant's assignees acknowledge their duty to replace the deposit should the depository be unable to furnish a sample when requested due to the condition of the deposit.

Example 1

Inhibition of transglutaminase activity

Thrombin-activated transglutaminase activity was measured by the method of Lorand et al. (Lorand L., Campbell-Wilkes V. K., Cooperstein L.: A filter paper assay for transamidating enzymes using radioactive amine substrates. Anal. Biochem. 50:623, 1972, herein incorporated by reference). The assay was modified for use in microtiter plates. In this assay, 50 µl of antibody solution (hybridoma supernatant or affinity-purified antibody) and 8 µl of heat-treated plasma were added to each well. After 30 min., 10 µl of thrombin (1.6 units), 10 µl of $CaCl_2$ (40 mM), and 10 µl of dithiothreitol (0.2M) were added to each well. After another incubation at 37° C. for 30 min., 25 µl of a mixture of $^{14}C$-putrescine (0.7 mmol; 50 µCi/ml) and casein (2.2%) was added. After an additional 30 minute incubation at 37° C., the reaction was terminated by the addition of 20 µl of iodoacetamide (1 mg/ml). A 20 µl aliquot of the reaction mixture was spotted on filter paper for detection of radioactivity.

Figure 2:
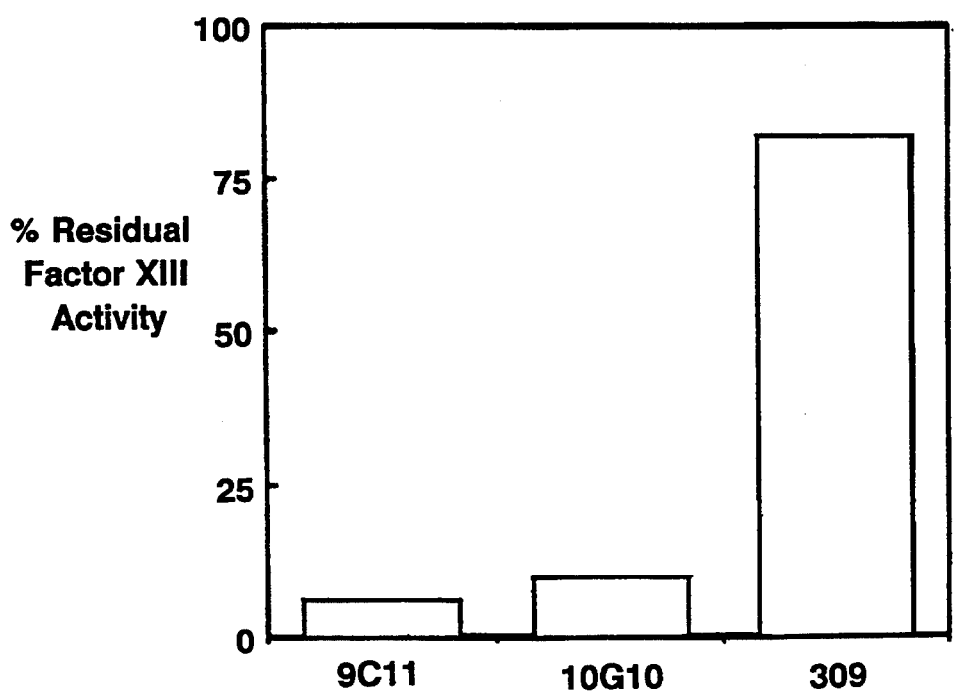
FIG. 2 is a bar graph showing the comparative effects of MAbs on FXIII activity. Equal concentrations of purified MAbs (0.1 mg/ml) were added to heat-treated plasma and resulting FXIII transglutaminase activity determined.

The effects of MAbs on FXIII activity was evaluated. The MAbs of the invention, 9C11 and 10G10, and MAb 309, an antipeptide MAb which is also specific for α2, were tested for the ability to inhibit transglutaminase activity as described above. As shown in FIG. 2, MAbs 9C11 and 10G10 were substantially more potent inhibitors of FXIII activity than MAb 309.

In some experiments, hybridoma supernatants were depleted of antibody by double-antibody precipitation. Briefly, 500 µl of hybridoma supernatant was mixed with 10 µl of affinity-purified rabbit anti-mouse antibody (2.8 mg/ml). After 30 min., 20 µl of affinity-purified goat anti-rabbit antibody (21.4 mg/ml) was added. After another 30 min., the mixture was placed on ice for 30 min. The immune complexes were precipitated by centrifugation at 12,000 rpm for 10 min. Antibody-depleted supernatant was then used in subsequent experiments. The goat anti-rabbit antibody and rabbit anti-mouse antibody were obtained from animals repeatedly immunized with the relevant immunoglobulin; the antibodies were affinity-purified on immunoglobulin coupled to agarose.

Culture supernatants from α2-specific antibody-producing hybridomas were tested to determine their effect on thrombin-activated transglutaminase activity. To evaluate immunoinhibition of α2, paired comparisons of hybridoma culture supernatants were made before and after they had been immunodepleted of MAb (TABLE 1). The apparent transglutaminase activity of MAb 9C11 supernatant was compared with that of two control supernatants (MAbs against fibrin and immunoglobulin kappa chain). Aliquots of culture supernatants from the two control MAbs and 9C11 were immunodepleted of monoclonal antibody by immunoprecipitation. Then culture supernatants before or after immunodepletion were incubated with plasma (8 µl), and the amount of thrombin-activated transglutaminase activity was determined by measuring the cross-linking of $^{14}C$-putrescine to casein. Mean±SD of duplicate observations is shown.

Before immunodepletion, there were notable differences among both control supernatants and 9C11. After immunodepletion, the transglutaminase activity of the control supernatants was unchanged, whereas that of the 9C11 supernatant doubled. This result indicated that antibody in the 9C11 culture supernatant had a direct inhibitory effect on α2. Using similar screening assays, another antibody, 10G10, was identified. This antibody also inhibited apparent transglutaminase activity.

TABLE 1

Transglutaminase Activity
(in picomoles of $^{14}$C-putrescine cross-linked)

| Monoclonal Antibody | Immunodepletion | |
| --- | --- | --- |
| | Before | After |
| Control 1 | 2.35 ± 0.06 | 2.35 ± 0.07 |
| Control 2 | 4.91 ± 0.19 | 4.56 ± 0.39 |
| 9C11 | 1.80 ± 0.12 | 3.96 ± 0.03 |

Figure 3:
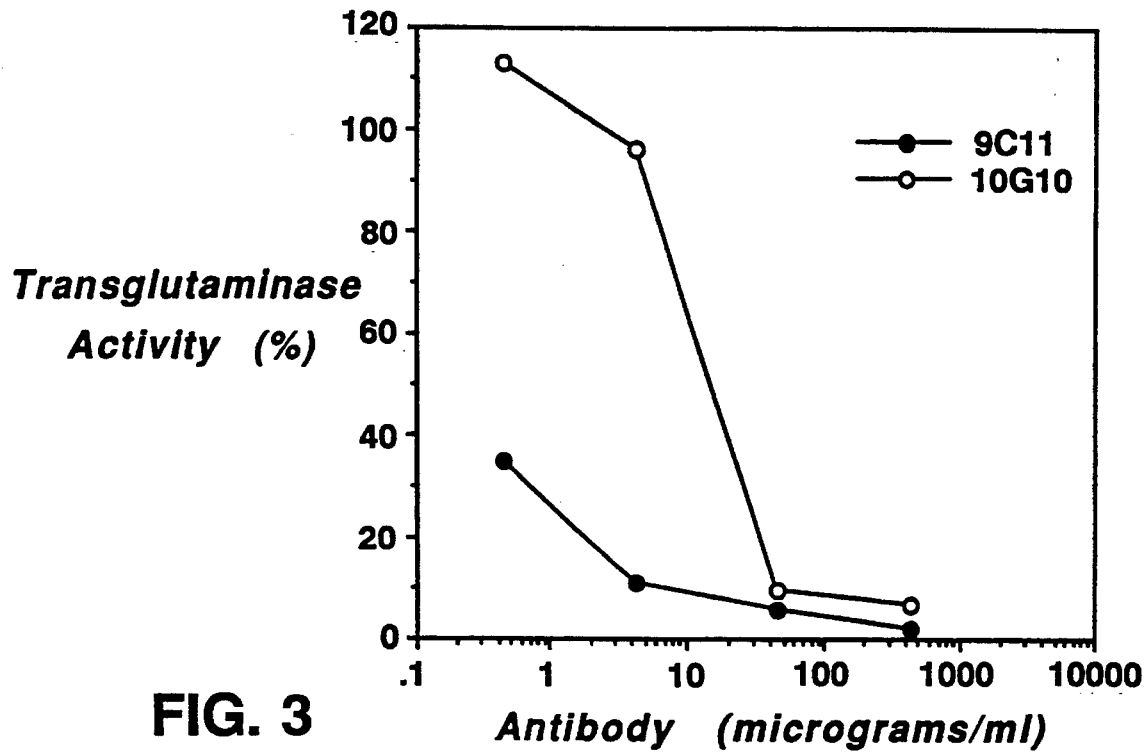
FIG. 3 is a line graph showing dose-related inhibition of FXIII transglutaminase activity. Heat-treated plasma (8 μl) was incubated with various concentrations of purified MAb 9C11 or MAb 10G10.

To confirm that MAbs 9C11 and 10G10 were inhibitors of α2, the dose-related effects of these purified MAbs on FXIII activity was evaluated. FIG. 3 shows that both MAbs inhibited apparent transglutaminase activity in a dose-related fashion. Compared with 10G10, 9C11 was a more potent inhibitor on a molar basis.

Example 2

Inhibition of fibrin crosslinking

Inhibition of fibrin cross-linking was measured as follows. Fresh-frozen plasma was mixed with trace amounts of $^{125}$I-human fibrinogen. 50 μl of MAb (1 mg/ml) was then added to 25 μl of the plasma/$^{125}$I-human fibrinogen. After 15 min., this mixture was transferred to glass tubes containing 25 μl of CaCl$_2$ and incubated at 37° C. for 10 min. The samples were then boiled for 5 min. and 100 μl of 9M urea with 2% dithiothreitol was added, followed by electrophoresis on 10% polyacrylamide gels. The gels were stained, dried, and autoradiographed on Kodak Xomat AR film, according to methods known in the art.

Figure 4:
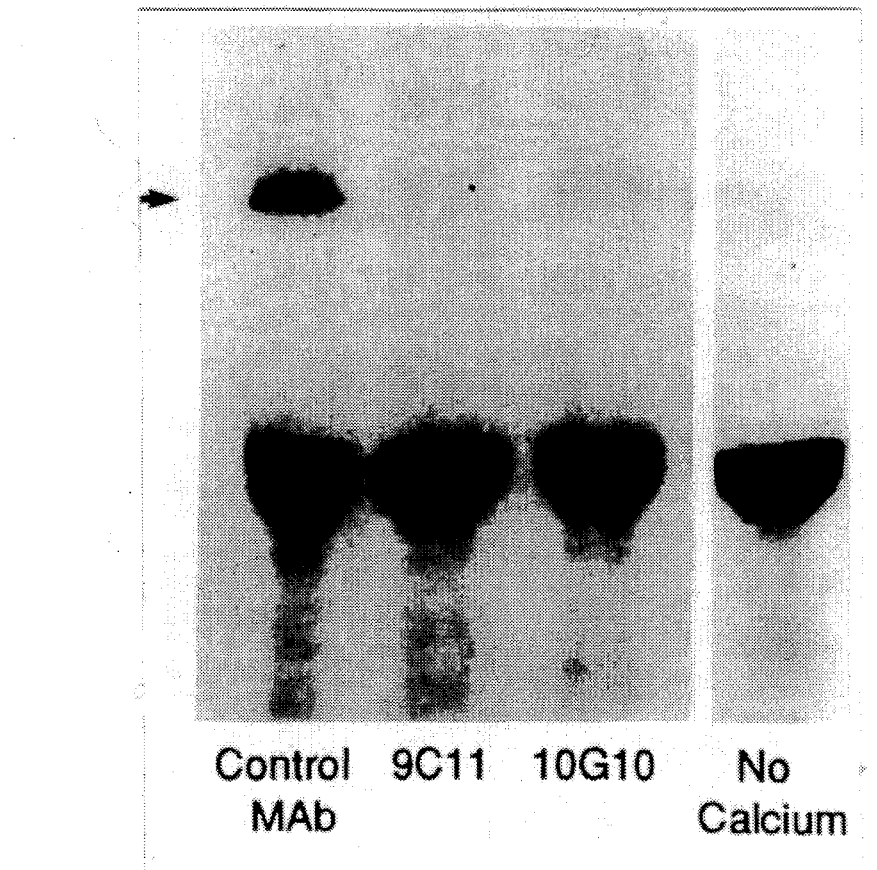
FIG. 4 is a photograph of an autoradiograph showing the effects of MAbs on fibrin cross-linking. MAb 9C11, MAb 10G10, or control (anti-digoxin) MAb was added to plasma containing trace amounts of radiolabeled fibrinogen. The plasma was clotted by recalcification. An unclotted plasma sample (no calcium) was used as a negative control. The clots were then analyzed by SDS-PAGE followed by autoradiography. The arrow indicates intermolecular cross-links between fibrin gamma chains.

In vivo, the chief physiologic substrate of FXIII is fibrin. When FXIII, fibrin, and thrombin interact with one another, FXIII cleavage by thrombin is accelerated. To determine whether the two MAbs inhibited the cross-linking of fibrin chains by FXIII in plasma, plasma clots were analyzed by SDS-PAGE (FIG. 4). Clots formed in the presence of the control MAb (anti-digoxin) showed clear evidence of fibrin gamma chain cross-linking, whereas clots formed in the presence of 10G10 and 9C11 showed no gamma chain dimer formation. Thus, even in plasma, MAbs 10G10 and 9C11 inhibited the formation of fibrin gamma chain crosslinks, the most efficient catalytic function of FXIII.

Example 3

Acceleration of clot lysis

Clot lysis was measured as follows. Fresh-frozen plasma was mixed with trace amounts of radiolabeled human fibrinogen (Reed G. L. III, Matsueda G. R., Haber E.: Synergistic fibrinolysis: combined effects of plasminogen activators and an antibody that inhibits α 2-antiplasmin. Proc. Natl. Acad. Sci. U.S.A. 87:1114, 1990, herein incorporated by reference). 50 μl of MAb (1 mg/ml) was incubated with 25 μl of plasma. After 15 min., the plasma was clotted by recalcification with 25 μl of CaCl$_2$ (40 mM) and incubated at 37° C. for 30 min. The clots were washed with 2 ml of Tris-buffered saline (TBS) containing 1 mg/ml iodoacetamide to stop cross-linking. The wash solution was removed and the clots evaluated for the incorporation of gamma radiation using a gamma counter. 200 μl of TBS containing 1 unit of urokinase was added to commence clot lysis. To determine the amount of lysis, the clots were incubated at 37° C. and 50 μl of supernatant was removed temporarily (for gamma counting) to measure the amount of soluble fibrin degradation products released into the supernatant.

By cross-linking α$_2$-antiplasmin to fibrin during clot formation, FXIII renders clots more resistant to lysis by plasminogen activators. Therefore, the effect of Mabs 9C11 and 10G10 on clot lysis was examined. MAbs 10G10 and 9C11 were found to accelerate the lysis of plasma clots, as measured in fibrinolysis experiments described below.

Figure 5:
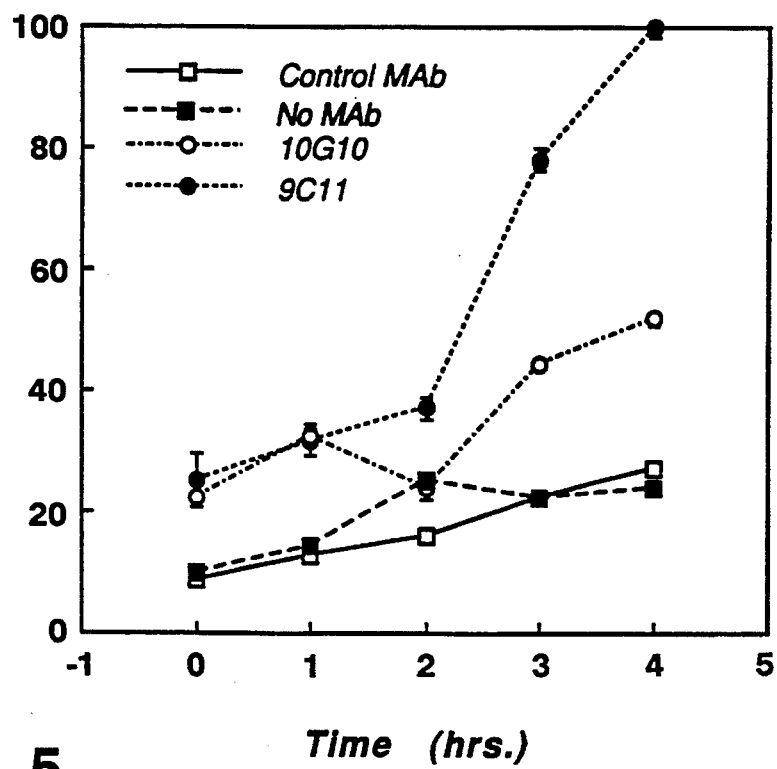
FIG. 5 is a line graph showing the effects of the MAbs of the invention on clot lysis. Plasma was mixed with trace amounts of radiolabeled fibrinogen and clotted in the presence of buffer (no MAb), a control MAb, 10G10, or 9C11. Urokinase (1 unit) was added to each clot and the amount of clot lysis was determined at hourly intervals. The data represent the mean and SD of duplicate observations.

FIG. 5 shows that clots formed with the control MAb, or in the absence of MAb, underwent a slow, progressive lysis over time. Clots formed with 10G10 underwent a more accelerated lysis, and clots formed with 9C11 dissolved even faster.

Example 4

Effect of MAbs on FXIII activation

The effect of MAbs on FXIII activation was measured as follows. Purified α2β2 (2 μg in 1 μl) (American Diagnostica, Greenwich, Conn.) was incubated with 50 μl of MAb (1 mg/ml) for 15 min. Thrombin (1 unit, 1 μl) was added and the mixture incubated at 37° C. for 30 min. 50 μl of sample buffer was added to each mixture and boiled for 3 min. The samples were analyzed by electrophoresis under reducing conditions on 7.5% gels and transfer to PVDF membranes by the semi-dry blotting method. The membranes were immunoblotted with an α2-specific MAb.

Figure 6:
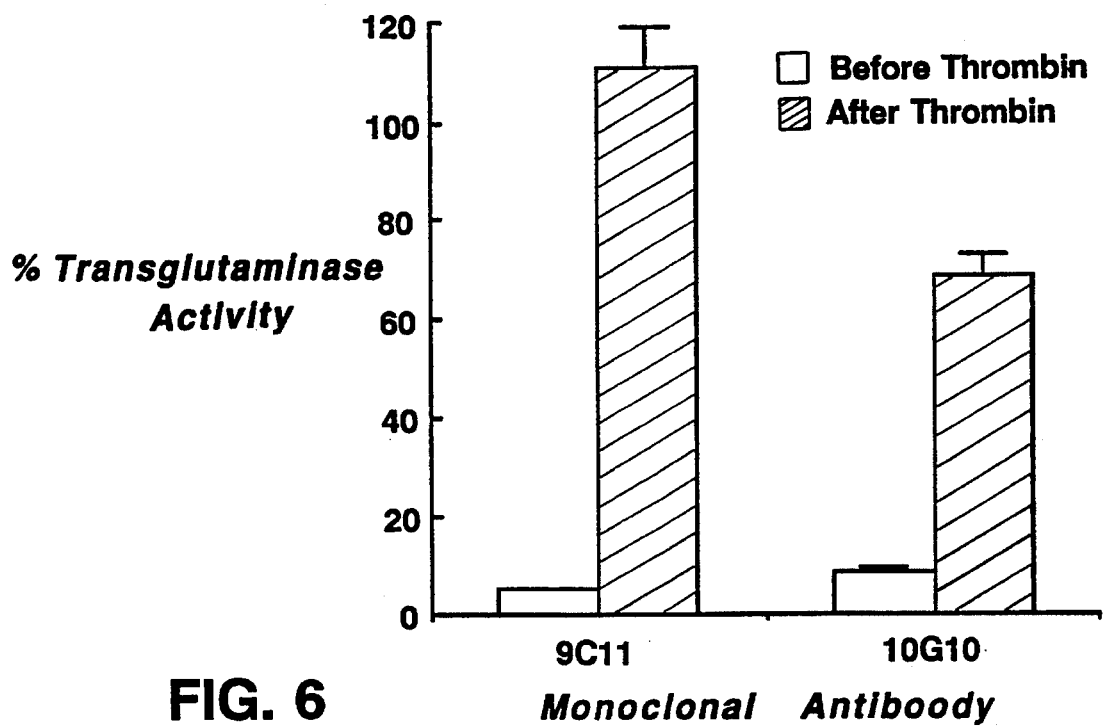
FIG. 6 is a bar graph showing the effects ot the MAb of the invention on FXIII activity. Purified MAb 9C11, 10G10, or no MAb, was added to heat-treated plasma before or after the addition of thrombin. The resulting transglutaminase activity was assayed. The mean standard deviation from duplicate observations is shown.
Figure 7:
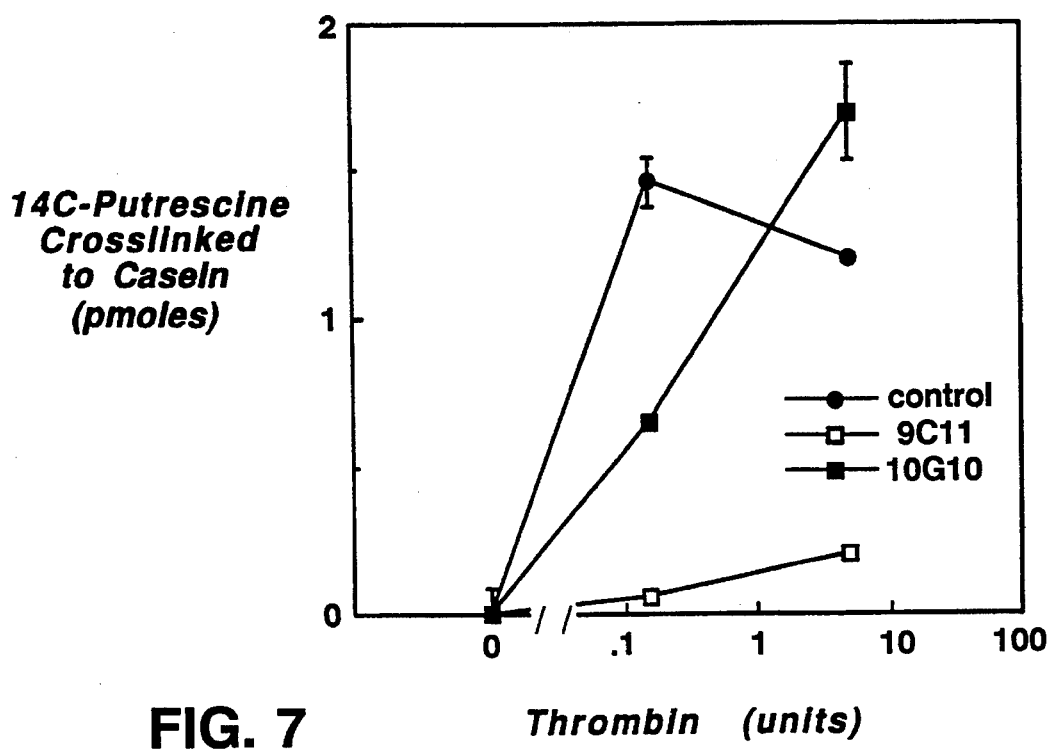
FIG. 7 is a line graph showing the effects of thrombin on FXIII inhibition by MAb 9C11 and 10G10. Two different doses of thrombin (0.156 and 5.0 U) were added to heat-treated plasma in the presence of no MAb, 9C11, or 10G10. The resulting transglutaminase activity was determined. The mean standard deviation from duplicate observations is shown.

To determine the mechanisms by which the two MAbs inhibited FXIII, FXIII was contacted with MAb before and after thrombin cleavage of FXIII. When FXIII was incubated with the MAbs prior to thrombin cleavage, both MAbs strongly inhibited subsequent transglutaminase activity (FIG. 6). When the MAbs were added after FXIII activation by thrombin, their inhibitory effects were diminished but still present (FIG. 6). These results suggest that the MAbs act to inhibit thrombin cleavage of α2 and that their inhibitory effects would be overcome, at least in part, by increasing the amount of thrombin in the activation mixture. FIG. 7 shows that increasing the amount of thrombin did indeed reduce the inhibitory effect of 10G10 and, to a lesser extent, that of 9C11. These results suggest that the two MAbs interfere with thrombin cleavage. In the control samples, the higher dose of thrombin (5 U) resulted in slightly less transglutaminase activity than the lower dose (0.16 U), suggesting that the higher dose of thrombin may inactivate FXIII by cleaving it at a second site in the molecule.

Figure 8:
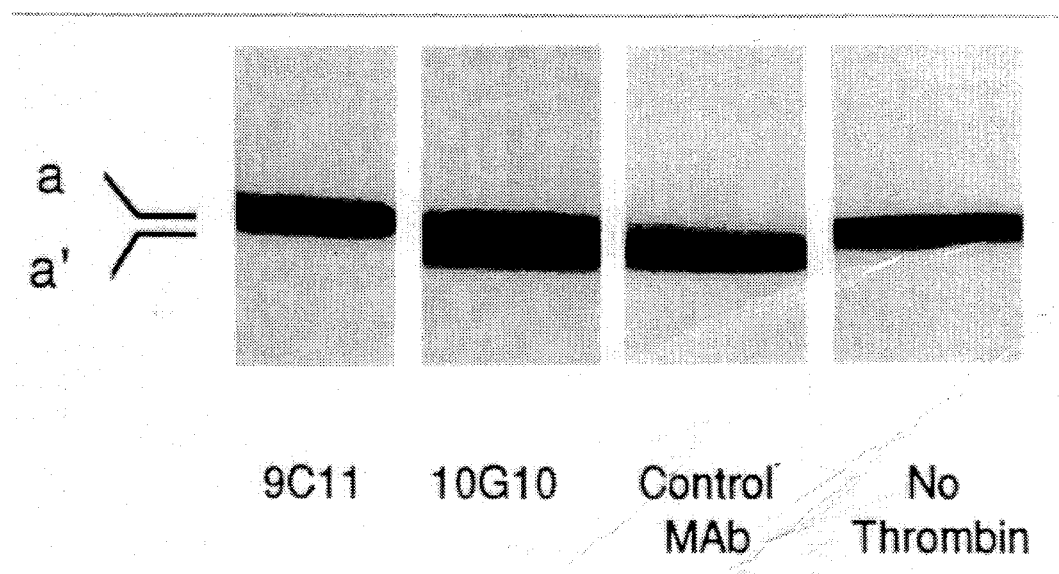
FIG. 8 is a photograph of an immunoblot showing the effects of the MAbs of the invention on thrombin cleavage of FXIII. Purified plasma FXIII was incubated with MAb 9C11, 10G10, or a control MAb, followed by the addition of thrombin. After incubation for 30 min., the samples were electrophoresed on 7.5% polyacrylamide gels and transferred to polyvinylidene difluoride (PVDF) membranes by electroblotting. Thrombin-cleaved FXIII, α2'and uncleaved FXIII, α2, were detected by immunoblotting.

Immunoblotting experiments were performed to test whether these MAbs inhibited thrombin cleavage of α2 to α2'. FXIII (β2) was incubated in the presence of thrombin and purified 9C11, 10G10, or a control MAb (anti-digoxin 40–160) for 30 min. at 37° C. The samples were then electrophoresed under denaturing conditions and immunoblotted with an antipeptide MAb, MAb 309, which is also specific for α2 (Lukacova D., Matsueda G. R., Haber E, Reed G. L.: Inhibition of factor XIII activation by an anti-peptide monoclonal antibody. Biochemistry 30:10164, 1991). FIG. 8 shows a comparison of data from each MAb. When no thrombin was present, no cleaved α2 (α2') was present. In the presence of the control MAb, thrombin cleaved most of the α2 to its slightly lower molecular weight form, α2'and only a faint band of residual α2 remained. Cleavage of α2 to α2' was less complete in the presence of 10G10, and in the presence of 9C11 there was little, if any, cleavage of by thrombin. Thus, as the previous experiments suggested, both MAbs acted to inhibit thrombin cleavage of FXIII.

Example 5

Specific Binding to FXIII

Competitive binding of MAbs was assayed as follows. Wells of a microtiter plate were coated with α2β2 (5 µg/ml, 50 µl). After nonspecific binding sites had been blocked with BSA, 25 µl of purified MAb (20 µg/ml) or 1% BSA was added to each well as an inhibitor. Radioiodinated MAb, [labeled by the Iodogen (Pierce, Rockford, Ill.) method (25 µl, 50,000 cpm)], was added to each well. After one hour of incubation, the plates were washed and radioactivity in each well measured using a gamma counter. The percentage of residual $^{125}$I-9C11 or $^{125}$I-10G10 binding to FXIII was computed for each unlabeled MAb which had been added as an inhibitor. Full or 100% binding represented binding observed in the absence of any inhibitor, and 0% binding was that observed in wells coated with BSA in the absence of FXIII.

Figure 9A:
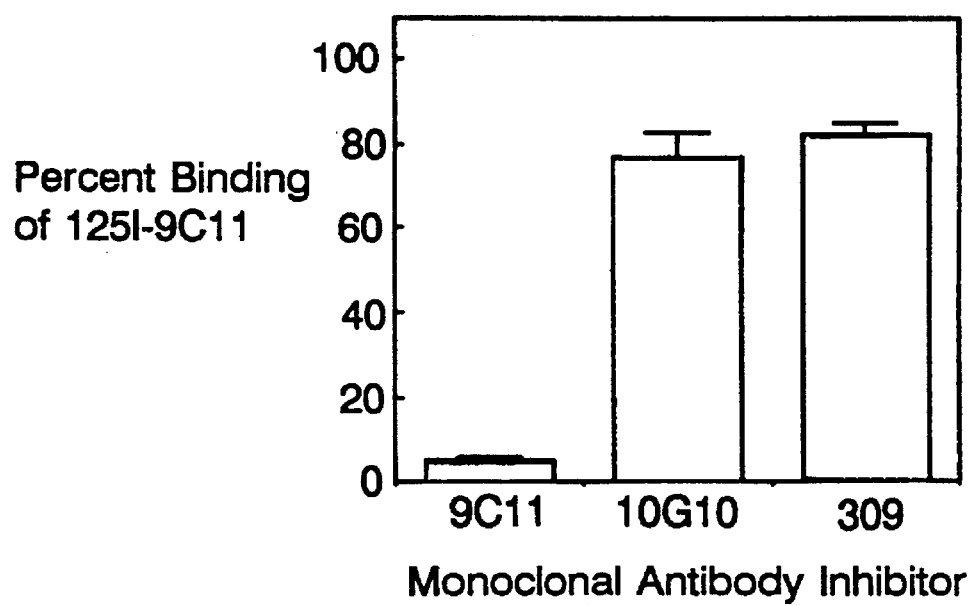
FIGS. 9A and 9B are bar graph; showing competitive binding of MAbs to FXIII. Wells of a microtiter plate were coated with purified plasma FXIII. Purified MAbs were added as inhibitors followed by $^{125}$I-9C11 (FIG. 9A) or $^{125}$I-10G10 (FIG. 9B). The amount of bound labeled MAb was determined by gamma counting. The data represent the mean standard deviation of at least two observations.
Figure 9B:
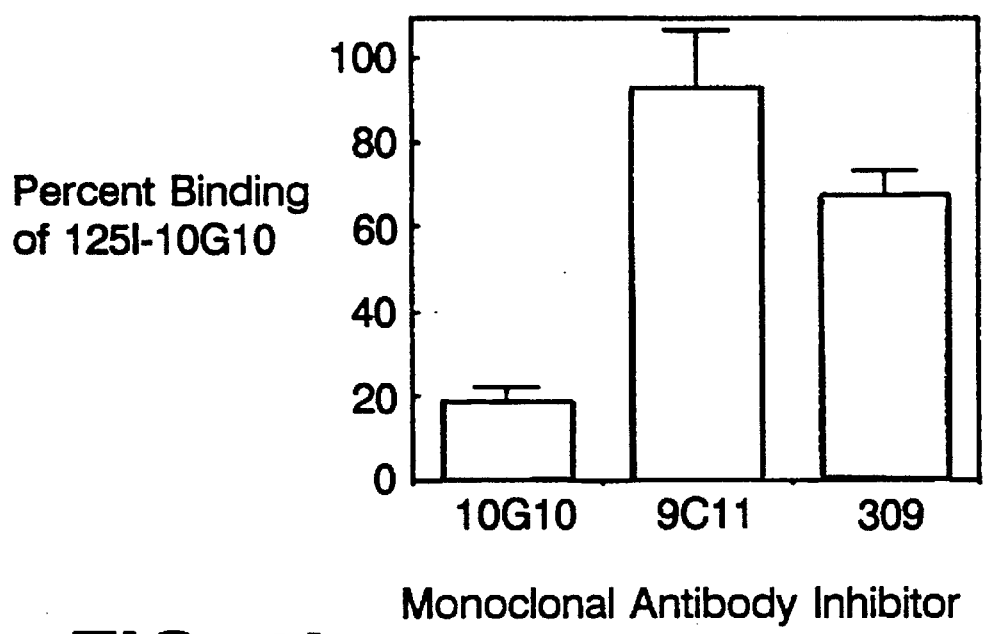

Competitive binding assays were performed to determine whether MAbs 9C11 and 10G10 bound to the same regions of the FXIII molecule. FXIII was immobilized in wells of a microtiter plate. Then $^{125}$I-9C11 or $^{125}$I-10G10 was added to the wells with a molar excess (more than 100 fold) of an unlabeled, purified MAb (309) as an inhibitor. FIG. 9 (left panel) shows the effects of various inhibitors on the binding of $^{125}$I-9C11 to immobilized FXIII. Unlabeled 9C11 almost completely inhibited the binding of $^{125}$-9C11 to FXIII, but 10G10 and 309 had little effect. FIG. 9 (right panel) shows the effects of the three inhibitors on the binding of 10G10 to FXIII. Again, unlabeled 10G10 strongly inhibited its own binding, whereas 9C11 had no effect and 309 had a minimal effect. These results indicate that MAbs 9C11 and 10G10 bind to separate or minimally overlapping regions of the FXIII molecule..

Example 6

Therapeutic prevention of blood clot formation

The compounds and methods of the invention are useful to prevent blood clot formation. Thrombotic disorders characterized by excessive or unwanted clotting of blood underlie a number of serious health threats, such as unstable angina and myocardial infarction. Other conditions which may indicate the administration of FXIII inhibitory compounds or antibodies of the invention include but are not limited to deep venous thrombosis, pulmonary thromboembolism, cerebral embolism, peripheral arterial occlusion and peripheral emboli in limbs. Stroke patients and patients recuperating from surgery, such as hip or back surgery, as well as patients confined to prolonged bed rest are at risk of developing undesirable thrombi, and thus, are candidates for therapeutic administration of FXIII-inhibitory compounds and antibodies of the invention.

For administration to human patients, immunoinhibitors of the invention, such as 9C11 or 10G10, can be humanized by methods known in the art, e.g, MAbs with a desired binding specificity can be commercially humanized (Scotgens, Scotland; Oxford Molecular, Palo Alto, Calif.). Monoclonal antibodies can be purified using known methods, such as absorption onto immobilized Protein A or immunoaffinity chromatography. Following purification, the immunoinhibitors of the invention or immunologically active fragments thereof, e.g., Fab, (Fab)$_2$, or Fv, can be administered to patients in a pharmaceutically acceptable excipient such as physiological saline. Immunoinhibitors of the invention can be administered by any standard route including intraperitoneally, intramuscularly, subcutaneously, or intravenously. It is expected that the preferred route of administration will be intravenous. Immunoinhibitors can be administered systemically to the bloodstream as well as locally within the blood vessel at the site of clot formation.

As is well known in the medical arts, dosages for any one patient depends on many factors, including the patients general health, sex, size, body surface area, age, as well as the particular compound to be administered, time and route of administration, and other drugs being administered concurrently. Dosages for the immunoinhibitors of the invention will vary, but a preferred dosage for intravenous administration is approximately 1 µg to 500 µg/ml/blood volume. Determination of correct dosage for a given application is well within the abilities of one of ordinary skill in the art of pharmacology.

The immunoinhibitors of the invention may also be administered simultaneously or sequentially with known thrombolytic agents. It is expected that simultaneous administration of immunoinhibitor and thrombolytic agent will be preferable. Preferred thrombolytic agents include plasminogen activators, e.g., urokinase, prourokinase, streptokinase, tissue-type plasminogen activator, staphylokinase or vampire bat tissue plasminogen activator, as well as physiologically active fragments thereof, e.g., single chain urokinase plasminogen activator (scu-PA) and hybrids, e.g., thrombolytic agents or active fragments thereof linked to an antibody, or mutant derivatives, e.g., those which include conservative amino acid substitutions. Thrombolytic agents are expected to be administered intravenously at approximately 0.1 to 2.0 mg per kg body weight. The dosage of immunoinhibitor to be co-administered with thrombolytic agent is approximately 1 µg to 500 µg/ml/blood volume, however as is well known in the art, the optimal dosage may be adjusted according to the condition of the patient and response of the patient to therapy.

Example 7

Detection of FXIII for diagnosis of disease

Congenital FXIII deficiency is rare and may be due to inadequate production of the enzyme or a gene mutation. Patients with FXIII deficiency have delayed hemorrhage following trauma and often have impaired wound healing. Umbilical hemorrhage is another symptom of inherited FXIII deficiency. In women with inherited FXIII deficiency, spontaneous abortion is common. In some cases, the hemorrhagic symptoms of FXIII deficiency arise in previously asymptomatic individuals. This acquired FXIII deficiency is typically the result of immunoinhibitors (in the form of autoantibodies) that impair FXIII function. Intracranial hemorrhage as a result of FXIII deficiency (inherited or acquired) is frequently fatal.

Frequently these immunoinhibitors occur in patients with multisystem disease and severe co-morbid illnesses as described by McDevitt et al. (McDevitt N. B., McDonagh J., Taylor H. L., Roberts H. R.: An acquired inhibitor to factor XIII. Arch. Intern. Med. 130:772, 1972), or in those who have received drugs such as isoniazid, phenytoin, and procainamide (see Otis P. T., Feinstein D. I., Rapaport S. I., Patch M. J.: An acquired inhibitor of fibrin stabilization associated with isoniazid therapy: clinical and biochemical observations. Blood 44:771, 1974; Fukue H., Anderson K., McPhedran P., Clyne L., McDonagh J.: A unique factor XIII inhibitor to a fibrin-binding site on factor XIIIA. Blood 79:65, 1992; Gailani D.: An IgG inhibitor against coagulation factor XIII: resolution of bleeding after plasma immunoadsorption with staphylococcal protein A (letter). Am. J. Med. 92:110, 1992). It is believed that these drugs induce immune intolerance of FXIII by chemical modification or by acting as haptens. The inhibition often appears to resolve with cessation of the drug.

Lorand et al. (Lorand L.: Hemorrhagic disorders of fibrin-stabilization, in Ogston D., Bennett B. (eds): Haemostasis: Biochemistry, Physiology and Pathology. London, John Wiley, 1977, p 405) classified these inhibitors into three groups. Group I inhibitors interfere with the activation of FXIII, Group II inhibitors neutralize activated FXIII (FXIIIa), and Group III inhibitors interfere with the interaction between FXIIIa and its substrate fibrin. Unfortunately, it is likely that many of these inhibitors are polyclonal (Krumdieck R., Shaw D. R., Huang S. T., Poon M-C, Rustagi P. K.: Hemorrhagic disorder due to an isoniazid-associated acquired factor XIII inhibitor in a patient with Waldenström's macroglobulinemia. Am. J. Med. 90:639, 1991) and bind to more than one epitope on FXIII. This explains the difficulty in establishing the precise mechanisms of FXIII inhibition and identifying the regions of FXIII to which the antibodies bind.

The lack of monoclonal antibodies of high affinity and appropriate specificity has thwarted diagnosis of FXIII abnormalities in patients. The invention provides potent and specific monoclonal antibodies for reliable and precise detection of FXIII. Using the methods of the invention, cost-effective and accurate diagnosis of FXIII deficiency can be accomplished. To detect FXIII in a sample, such as patient blood, an inhibition assay can be performed. For example, a sample in a test tube or vessel coated with FXIII antigen is incubated with a FXIII-specific MAb, e.g., 9C11 or 10G10. The unbound antibody washed away and the FXIII-specific antibody bound to the test tube or vessel is detected using any label or method of labelling of antibodies known in the art, e.g., enzymes, radioisotopes, fluorescent compounds and metal chelates. For example, the antibodies of the invention can be used in an enzyme-linked immunosorbent assay (ELISA) to detect FXIII in samples. The amount of bound antibody is compared to a standard curve in which the amount of antibody binding is plotted against a known amount of FXIII. Alternatively, a "capture/tag" assay can be performed in which FXIII is captured using one antibody and tagged or detected using a second antibody may also be used. This method may offer the advantage of increased sensitivity in the detection of low levels of FXIII.

The antibodies of the invention can also be used to determine the specificity of spontaneously occurring FXIII inhibitors. A competition assay can be constructed in which FXIII is contacted with a sample containing a spontaneously or naturally-occurring inhibitor, e.g., patient serum, and the ability of an antibody of known specificity, e.g., 9C11 or 10G10, to compete for FXIII binding evaluated. Binding of the antibody of the invention can be detected using labelling techniques known in the art, as described above. Binding of the known FXIII-specific antibody to FXIII in the presence of a patient sample indicates that the naturally-occurring inhibitor has a binding specificity distinct from that of the antibody, whereas reduced binding may indicate that the binding specificity of the naturally-occurring inhibitor is identical or closely related to that of the known FXIII-specific antibody of the invention.

Example 8

Identification of novel immunoinhibitors

Candidate compounds can be screened for FXIII inhibitory activity by identifying those which block the binding of a FXIII-specific monoclonal antibody which does not bind to the thrombin cleavage site, e.g., MAb 9C11 or MAb 10G10, using a competitive binding assay (see Example 5). Compounds which block binding of such a MAb, e.g., 9C11 or 10G10, bind to FXIII at or near the epitope to which the MAb binds to FXIII. Compounds identified in this manner are thus likely to inhibit the activity of FXIII in the same manner as the MAb. Since 9C11 and 10G10 inhibit the activity of FXIII even after activation by thrombin cleavage, the screening assay can also be used to identify compounds which block the binding of these MAbs to activated FXIII. The FXIII-inhibitory activity of compounds identified using the screening assay of the invention can then be further characterized and confirmed using assays and procedures described in Examples 1–5.

ADVANTAGES

The difficulty in generating high-affinity MAbs specific for FXIII has been discussed above. When animals were immunized with β2, the vast majority of MAbs obtained were against the β subunit of FXIII. Subsequent fusion experiments yielded primarily low-affinity MAbs of the IgM isotype. As detailed above, conventional immunization protocols did not yield monoclonal antibodies of the appropriate specificity and potency. It was found that only with a schedule of repeated immunization over a prolonged period was it possible to produce antibodies of high affinity and specificity. MAbs 9C11 and 10G10 bind specifically to FXIII with high affinity and represent the most potent inhibitors of thrombin-initiated activation of the FXIII zymogen known. With the guidance provide herein, one of ordinary skill should be readily able to repeat the successful experiments disclosed herein, and develop additional MAbs of the invention which would be expected to exhibit similar or even greater FXIII-inhibitory activity than MAbs 9C11 and 10G10.

The immunoinhibitors of the invention provide many advantages over inhibitors of blood coagulation in the prior art. In addition to the therapeutic applications discussed above, these compostions can be used as specific probes for identifying the acquired FXIII inhibitors that develop in patients, and they may be useful tools for analyzing FXIII function in vivo. Although both MAbs were raised against platelet FXIII, they also bind well to plasma FXIII. Also, both MAbs reduced the thrombin-activatable transglutaminase activity of FXIII and inhibited the formation of fibrin gamma chain cross-links, the fastest of FXIII's enzymatic functions.

The two MAbs were most potent at inhibiting FXIII when they were present during rather than after thrombin activation. However, the immunoinhibitors of the invention also inhibited transglutaminase activity even after FXIII was activated by thrombin cleavage, a significant and unexpected result.

The immunoinhibitors inhibit thrombin cleavage of the α-subunit without binding to the thrombin cleavage site. Also, as discussed above, the immunoinhibitors bind only to native FXIII. It is possible that 9C11 or 10G10 interferes with FXIII cleavage by sterically hindering the binding of thrombin to the zymogen, or by allosterically modifying FXIII so that is a much less efficient thrombin substrate.

In addition, these novel immunoinhibitors not only prevent FXIII-catalyzed formation of blood clots, they accelerate the lysis of blood clots, thereby making these immunoinhibitors ideal therapeutic agents for treatment of patients with aberrant or excessive blood clots and those at risk of developing unwanted blood clots. It is believed that by inhibiting the crosslinking of α2-antiplasmin to fibrin and fibrin chains to one another, the immunoinhibitors of the invention render fibrin clots markedly susceptible to degradation by plasmin. Thus, they amplify the effects of fibrinolytic agents.

Other Embodiments

Also within the invention are analogs of the immunoinhibitors of the invention.

Analogues can differ from the native proteins or peptides by amino acid sequence, or by modifications which do not affect the sequence, or by both. Modifications (which do not normally alter primary sequence) include in vivo or in vitro chemical derivitization of polypeptides, e.g., acetylation or carboxylation of the termini.

The invention also includes analogs in which one or more peptide bonds have been replaced with an alternative type of covalent bond (a "peptide mimetic") which is not susceptible to cleavage by peptidases. Where proteolytic degradation of the peptides following injection into the subject is a problem, replacement of a particularly sensitive peptide bond with a noncleavable peptide mimetic will make the resulting peptide more stable and thus more useful as a therapeutic. Such mimetics, and methods of incorporating them into polypeptides, are well known in the art. Similarly, the replacement of an L-amino acid residue is a standard way of rendering the polypeptide less sensitive to proteolysis. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl.

In addition to identifying other immunoinhibitors of FXIII activity, the screening methods of the invention can be used to identify peptide and non-peptide inhibitors. For instance, the screening methods of the invention can first be used to identify peptides which are capable of inhibiting FXIII activity. The three-dimensional structure of these peptides can be determined by methods known in the art, e.g., 3-D nuclear magnetic resonance analysis. The structure of inhibitory peptides can then be compared to the structures of non-peptide compounds to identify compounds having a structure similar or identical to that of the inhibitory peptide. FXIII inhibitory activity of such compounds could be further characterized as described in Examples 1–5. Non-peptide compounds with FXIII inhibitory activity, identified as described above, or by direct screening using the assay of the invention, can be administered to patients as described above.

What is claimed is:

1. A monoclonal antibody which inhibits the ability of Factor XIII to catalyze the formation of a blood clot, wherein said antibody inhibits thrombin cleavage of said Factor XIII but does not bind to the thrombin-cleavage site of said Factor XIII, wherein said antibody binds to the same epitope on Factor XIII as antibodies selected from the group consisting of 9C11 produced by the hybridoma having the accession number ATCC CRL 11458 and 10G10 produced by the hybridoma having the accession number ATCC CRL 11457.

2. The monoclonal antibody of claim 1, wherein said antibody is selected from the group consisting of 9C11 produced by the hybridoma having the accession number ATCC CRL 11458 and 10G10 produced by the hybridoma having the accession number ATCC CRL 11457.

* * * * *

UNITED STATES PATENT AND TRADEMARK OFFICE
CERTIFICATE OF CORRECTION

PATENT NO. : 5,470,957             Page 1 of 2
DATED : November 28, 1995
INVENTOR(S) : Guy Reed It is certified that error appears in the above-indentified patent and that said Letters Patent is hereby corrected as shown below:

Cover page, under [56] References Cited, OTHER PUBLICATIONS, the second "Godal" reference, "Haemtol." should be --Haemotol.--.

Cover page, under [56] References Cited, OTHER PUBLICATIONS, the "Lorand" reference, "Stablizing" should be --Stabilizing--.

Cover page, under [56] References Cited, OTHER PUBLICATIONS, the "Lorand" reference, after "Amine", delete the comma.

Cover page, under [56] References Cited, OTHER PUBLICATIONS, the "Reed" reference, "Fibinolysis" should be --Fibrinolysis--.

Cover page, under [56] References Cited, OTHER PUBLICATIONS, the "Rosenberg" reference, "26269-284" should be --26:269-284--.

Cover page, under [56] References Cited, OTHER PUBLICATIONS, the "Sakata" reference, "Fibrin-stablizing" should be --Fibrin-stabilizing--.

Cover page, under [56] References Cited, OTHER PUBLICATIONS, the "Schlaeger" reference, "146111-120" should be --146:111-120--.

FIG. 6, Sheet 3 of 5, "Antiboody" should be --Antibody--.

Col. 1, line 11, after "relates", delete the semicolon.

Col. 2, line 54, "e.g" should be --e.g.--.

UNITED STATES PATENT AND TRADEMARK OFFICE
CERTIFICATE OF CORRECTION

PATENT NO. : 5,470,957
DATED : November 28, 1995
INVENTOR(S) : Guy Reed

It is certified that error appears in the above-indentified patent and that said Letters Patent is hereby corrected as shown below:

Col. 3, line 42, "ot" should be --of--.

Col. 3, line 65, "graph;" should be --graphs--.

Col. 5, line 38, delete the second occurrence of "was".

Col. 7, under Table 1, the text is printed too small.

Col. 7, line 66, "α 2-antiplasmin" should be --α2-antiplasmin--.

Col. 8, line 17, "Mabs" should be --MAbs--.

Col. 9, line 48, after "molecule" delete the second period.

Col. 10, line 6, "Scotgens" should be --Scotgene--.

Col. 12, line 47, "provide" should be --provided--.

Col. 12, line 56, "compostions" should be --compositions--.

Signed and Sealed this

Thirtieth Day of April, 1996

Attest:

BRUCE LEHMAN

*Attesting Officer*     *Commissioner of Patents and Trademarks*